United States Patent [19]

Dawson et al.

[11] Patent Number: 5,545,761

[45] Date of Patent: Aug. 13, 1996

[54] METHOD OF MAKING KETOISOPHORONE VIA OXIDATION OF ISOPHORONE WITH TERT-BUTYL HYDROPEROXIDE

[75] Inventors: Bryan T. Dawson; Joseph Pugach, both of Monroeville Boro, Pa.

[73] Assignee: Aristech Chemical Corporation, Pittsburgh, Pa.

[21] Appl. No.: 337,716

[22] Filed: Nov. 14, 1994

[51] Int. Cl.$^6$ .......................... C07C 45/28; C07C 45/34
[52] U.S. Cl. ............................... 568/342; 568/343
[58] Field of Search ......................... 568/342, 343

[56] References Cited

U.S. PATENT DOCUMENTS

| | | | |
|---|---|---|---|
| 3,931,327 | 1/1976 | Strickler et al. | 260/586 P |
| 3,944,620 | 3/1976 | Becker et al. | 260/586 P |
| 3,960,966 | 6/1976 | Widmer et al. | 260/586 P |
| 4,898,984 | 2/1990 | Bellut | 568/342 |

OTHER PUBLICATIONS

Hosokawa et al., *Chemistry Letters*, pp. 1081–1082 (1983).
CA112: 76460b (1990).
Holland et al., *Can. J. Chem.*, vol. 60, pp. 1919–1923 (1982).

Primary Examiner—Gary Geist
Assistant Examiner—Barbara S. Frazier
Attorney, Agent, or Firm—William L. Krayer; Robert R. Gavlik

[57] ABSTRACT

A method of manufacturing 2,6,6-trimethyl-2-cyclohexen-1,4-dione (ketoisophorone) from 3,5,5-trimethyl-2-cyclohexenone (alpha-isophorone). The alpha-isophorone is reacted with hydroperoxide in a solvent, and in the presence of a metal catalyst. The reaction converts the alpha-isophorone directly to ketoisophorone without the intermediate isomerization of alpha-isophorone to beta-isophorone (3,5,5-trimethyl-3-cyclohexenone).

13 Claims, No Drawings

METHOD OF MAKING KETOISOPHORONE VIA OXIDATION OF ISOPHORONE WITH TERT-BUTYL HYDROPEROXIDE

TECHNICAL FIELD

This invention relates to a method of manufacturing ketoisophorone (2,6,6-trimethyl-2-cyclohexen-1,4-dione, herein referred to as "KIP"). The method involves the direct oxidation of alpha-isophorone (3,5,5-trimethyl-2-cyclohexenone, herein referred to as "alpha-IP") with a hydroperoxide in a solvent system, and in the presence of a metal catalyst.

BACKGROUND OF THE INVENTION

Ketoisophorone is valued as an intermediate in the production of drugs and perfumes, and can be obtained via the oxidation of alpha-IP (by alpha-IP applicants mean isophorone that is predominately or completely in the alpha form). Numerous procedures have been developed to accomplish this oxidation. In U.S. Pat. No. 3,931,327 a two step process was used to convert isophorone to KIP. The first step is the conversion of alpha-IP to its isomeric form, beta-IP (3,5,5-trimethyl-3-cyclohexenone). In the second step, the beta-IP is converted to KIP by passing molecular oxygen through the beta-IP in the presence of a metal catalyst and an organic base. However, this process has the disadvantage of indirect conversion of alpha-IP to KIP as well as lower efficiency and selectivity attributable to the oxidant used.

In U.S. Pat. No. 3,960,966, Widmer et al disclose a process of manufacturing KIP by the oxidation of alpha-IP. The reaction takes place in an oxygen atmosphere and a metal catalyst is used. This invention differs from applicants' in that hydroperoxides are not employed. Lower selectivity is achieved here, and unwanted side products result. Also, this process suffers in that large amounts of catalyst (a significant portion of which is not retrievable) must be employed.

In U.S. Pat. No. 3,944,620, Becker et al disclose a process for preparing KIP from alpha-IP. Here as well, the oxidant is gaseous oxygen and a metal catalyst is employed. The process occurs, at least in part, by the two-step process described above. Unlike applicants' invention, this process also suffers from low efficiency.

In recent years, hydroperoxides have been used in the production of specialty organic chemicals. These oxidants often provide more efficient and selective oxidation reactions. Higher selectivity reduces or eliminates the generation of various side-products. These side-products can affect processing, product purity, and may raise other environmental concerns.

Reactions using tert-butyl hydroperoxide ("TBHP") as an oxidant in KIP production have been reported by Hosokawa et al in Chem. Lett., pp. 1081–1082 (1983). The reactions were catalyzed by $Pd(OAc)_2$ in an air atmosphere. Benzene was used as a solvent.

The present invention is an improved method of alpha-IP to KIP synthesis. The reaction is a one step process in which the isomerization of alpha-IP to beta-IP has been eliminated. Hydroperoxides have proven to be effective oxidants. Applicants catalysts and solvent systems have likewise proven to be a significant improvement in the art. Applicants have solved the problems of inefficiency and low selectivity associated with KIP synthesis in the prior art.

SUMMARY OF THE INVENTION

We have invented a method of producing 2,6,6-trimethyl-2-cyclohexen-1,4-dione from alpha-isophorone (3,5,5-trimethyl-2-cyclohexenone). This process features the direct conversion of alpha-IP to KIP. There is no need for the intermediary isomerization to beta-isophorone (3,5,5-trimethyl-3-cyclohexenone). The oxidation reaction employs a hydroperoxide, a catalyst, and a solvent system.

Alpha-IP can be reacted with hydroperoxide delivered as a wet solution (about 20–30% water). However, results with wet solutions are not entirely satisfactory.

It is preferable to deliver the hydroperoxide as a dried solution. Any acceptable manner of azeotropically drying the hydroperoxide solution can be used. Applicants use hydroperoxides having a concentration of up to 5 mol/L. Preferably 3.0 to 3.3 mol/L is used. The hydroperoxide could be delivered as a more concentrated solution, but for safety reasons it is diluted. Equivalents of hydroperoxide to alpha-IP can range from 2 to 4:1, with 2.2 to 2.4:1 being preferred. Applicants' preferred hydroperoxide is tert-butyl hydroperoxide. Solvents used to deliver the hydroperoxide include, but are not limited to the following: toluene, cyclohexane, ethyl acetate, tert-butyl alcohol, methylene chloride, 1,2-dichlorobenzene and 2,2,4-trimethylpentane.

Any oxidation resistant solvent can be used. By oxidation resistant, applicants mean any solvent that resists oxidation under the reactor conditions employed by applicants. Reactions can be run with any one of the following: toluene, cumene, chlorobenzene, methylene chloride, carbon tetrachloride, 1,2-dichloroethane, chloroform, pyridine compounds, and acetonitrile. Of these, toluene, cumene, acetonitrile, chlorobenzene, chloroform and pyridine compounds are favored.

The presence of a pyridine compound provides a significant effect in product selectivity, and can comprise 10 to 100% of the solution medium. Applicants prefer a reaction solvent comprising a pyridine compound and acetonitrile ("ANP"). Most preferably, an ANP solvent comprising about 10 to 30 vol % of a pyridine compound is used. The concentration of alpha-IP in the total reaction volume is not crucial, but should run preferably in the range of about 0.5 mol/L.

The catalyst employed in the above system is a metal compound selected from groups IB, VB, VIB, or VIII. Preferred catalysts include the following: CuCl, Cu(II) phthalocyamine, Cu(I) [dipyridyl]$_2$ClO$_4$, RuCl$_3$.3H$_2$O, V$_2$O$_5$, pyridine dichromate ("PDC") and FeCl$_3$. Concentrations of the metal catalyst vary depending on the particular complex, but typically range from 0.5 to 5 mol % of isophorone.

Reaction temperatures typically can range from 50° to 70° C. and reaction times can be run from 0.5 to 5 days. Applicants found reaction times in the range of 2 to 3 days to be preferable for highest conversions without loss of selectivity.

DETAILED DESCRIPTION OF THE INVENTION

Yields of KIP were generally more favorable when run under an oxygen atmosphere. The extent of this advantage varied with the metal catalyst. For example, with CuCl an additional 7% yield was obtained when the reaction was run under an oxygen atmosphere compared to argon (see Table I, entries 7 and 8). Pyridinium dichromate ("PDC") and RuCl$_3$ catalyzed reactions achieved improved yields as well. In contrast, PDC suffered considerable loss in KIP yield when run under argon (Table III, entries 4 and 5), and RuCl$_3$ suffered similar losses in efficiency when run under an atmosphere of air (Table III, entries 11 and 12).

Yields of KIP were comparable in a CuCl-catalyzed oxidation, regardless of the source of hydroperoxide (see entries 11–13 of Table I). All the reactions were stirred in an ANP solvent under an oxygen atmosphere, and were heated to 50° C.

Applicants generated worthwhile quantities KIP from an iron-catalyzed system. The majority of solvents for the reaction with TBHP (2 equiv.) and FeCl$_3$.6H$_2$O (4 mol %), led to a mixture of alpha-IP-oxidized products, see entries 1, 10–13, Table II. Possible by-products include the allylic alcohol and tert-butyl hydroperoxide product of alpha-IP ("BHPIP"). The ANP solvent contributed to the discrete formation of KIP. If the alcohol or BHPIP by-products form in the ANP solvent, the alcohol and peroxide may be readily oxidized to KIP under the reaction conditions.

The overall selectivities in the Fe$^{+3}$-catalyzed reactions were typically 60%. As shown in Table II, entry 3, yields of KIP could reach as high as 48% when alpha-IP was oxidized with TBHP in a dichloroethane azeotrope (2 equiv, 3.3M), with FeCl$_3$.6H$_2$O and ANP solvent. The reaction was stirred under an oxygen atmosphere for 2 days at 50° C.

Another reaction, Table II, entry 5, involved the total addition of 4 equivalents of TBHP. Additions were incremental over a 3 day period. Conversions of alpha-IP increased with each addition, however, selectivity dropped from 61 to 46%. Yields of KIP remained in the 45% range, and it was concluded that excess oxidant does not provide enhanced yields of KIP.

Applicants tested other metal catalysts. Two successful chromium catalysts are PDC [(pyH)$_2$Cr$_2$O$_7$]and pyridinium chlorochromate ("PCC"),[(pyH)ClCrO$_3$]. An initial reaction with PDC (Table III, entry 3) produced a 25% yield of KIP. With a smaller charge of catalyst (0.5 mol %), PDC provided favorable results with a 71% selectivity and a 46% yield. PCC did not promote TBHP decomposition as readily as PDC, however, the selectivity and yield of KIP were diminished to 60 and 30% respectively (see Table III, entry 8).

A RuCl$_3$.3H$_2$O catalyst, with a 0.5 mol % charge reacted with little TBHP decomposition. Temperatures of approximately 70° C. were required for conversion to proceed within a reasonable time. KIP yields in the range of about 40% were obtained.

A vandium-based catalyst was developed from V$_2$O$_5$. The first reaction was with an ANP solvent system, see Table III, entry 14. The KIP yield was 17%. The addition of 20 mol % picolinic acid, and the omission of pyridine as a cosolvent yielded 26% KIP. Selectivity of KIP was poor here. A reaction with the picolinic acid additive and ANP solvent provided a 43% KIP yield, and selectivity improved into the mid-60% range.

The invention is illustrated by, but not limited to the following example.

A 250-ml, 3-neck roundbottom flask was equipped with a condenser, gas inlet valve, and Teflon stir bar. Pyridinium dichromate (PDC, 0.25 mmol) was charged into the flask prior to the flask being sealed with a septum. The flask was evacuated and refilled with an oxygen atmosphere. The top of the condenser was connected to an oil bubbler and a slight positive pressure of O$_2$ was maintained throughout the experiment. A 50-ml dropping funnel was inserted between the septum and the flask. The flask was charged with pyridine (11 ml), acetonitrile (45 ml), and IP (50.6 mmol). Chlorobenzene (30.5 mmol) was included as an internal standard for GC analysis and its presence does not alter the chemistry. A previously prepared 3.3M solution of TBHP (34 ml, 112 mmol) was added dropwise to the stirring reaction mixture at room temperature. After 20 minutes, the flask was gradually heated and the temperature of the reaction was monitored with a thermometer.

Aliquots (2 ml) were periodically removed from the flask and quenched with 20% aqueous H$_2$SO$_4$(5 ml). The quench was extracted with diethyl ether (3×4 ml) and the combined organics were dried over MgSO$_4$ prior to injection on the GC. Response factors for the reaction components had been previously calculated from standards containing analytically pure alpha-IP, KIP and chlorobenzene. Results of conversion (C), selectivity (S) and yield (Y) of KIP were determined.

The reaction mixture was quenched with 20% aqueous H$_2$SO$_4$ on the small scale. The excess TBHP could have also been reduced with aqueous solutions of sodium sulfite (Na$_2$SO$_3$, preferred) or sodium bisulfite (NaHSO$_3$, less preferred).

| Q | (time, temp) | C | S | Y |
|---|---|---|---|---|
| 1 | (4 h, 30° C.) | 18 | 72 | 13 |
| 2 | (20 h, 30° C.) | 38 | 74 | 28 |
| 3 | (2 d, 30° C.) | 54 | 67 | 36 |
| 4 | (3 d, 50° C.) | 65 | 71 | 46 |

TABLE I

Ketoisophorone Synthesis Via Oxidation of Isophorone With TBHP.

| | Catalyst[a] | Solvent[b] | TBHP[c] | % KIP[d] | Notes |
|---|---|---|---|---|---|
| 1 | Pd(OAc)$_2$ | PhH | A | 19 | 50° C., 2 d |
| 2 | Pd(OAc)$_2$ | PhMe | A | 24 | 50° C., 2 d |
| 3 | CuCl | PhMe | B | 6 | not selective |
| 4 | CuCl | DCE | C | 20 | Ar atm, 50° C., 1 d |
| 5 | CuCl | DCE | C | 40 | beta-IP, 1,2-diketone[e] |
| 6 | CuCl | DCE | C | 25 | 4 equiv TBHP, Ar atm, 50° C. |
| 7 | CuCl | PhCl | D | 30 | Ar atm, 50° C., 2 d |
| 8 | CuCl | PhCl | D | 37 | O$_2$ atm, 50° C., 2 d |
| 9 | CuCl | PhCl | D | 0 | Et$_3$N,[f] TBHP decomp |
| 10 | CuCl | PhCl | D | 43 | MgSO$_4$,[g] O$_2$ atm |
| 11 | CuCl | ANP | B | 34 | O$_2$ atm, 50° C., 2 d |
| 12 | CuCl | ANP | E | 30 | O$_2$ atm, 50° C., 2 d |
| 13 | CuCl[h] | ANP | C | 45 | O$_2$ atm, 50° C., 5 d |
| 14 | CuCl[i] | ANP | C | 33 | O$_2$ atm, 2 d |
| 15 | CuCl[j] | ANP | C | 42 | Dp,[k] O$_2$ atm, 50° C., 3 d |
| 16 | CuCl[j] | MeCN | C | 34 | Dp,[k] O$_2$ atm, 60° C., 3 d |
| 17 | CuCl | DCE | C | 39 | O$_2$ atm |
| 18 | CuPhth[l] | ANP | C | 27 | O$_2$ atm, 50° C., 2 d |
| 19 | CUCN | ANP | E | 19 | O$_2$ atm, 50° C., 2 d |
| 20 | CuDp$_2$[m] | ANP | E | 29 | O$_2$ atm, rt, 1 d |
| 21 | CuDp$_2$[m] | ANP | E | 25 | O$_2$ atm, rt, 1 d |

[a]Palladium and copper were used as a 10 mol % catalyst in respect to IP, unless otherwise noted.
[b]PhH = benzene; PhMe = toluene; DCE = 1,2-dichloroethane; PhCl = chlorobenzene; ANP = MeCN and pyridine in a 4:1 v/v ratio, respectively; MeCN = acetonitrile.
[c]TBHP was added as: A = in PhH; B = 90%, 5% water, 5% t-BuOH; C = in DCE; D = in PhCl; E = in 2,2,4-trimethylpentane. TBHP in solvents were azeotropically dried and stored as 3.0–3.3 M solutions in the refrigerator. In the reaction, 2.2 equiv of TBHP were reacted with 1 equiv of IP.
[d]Yields determined by GC analysis.
[e]40% charged IP was beta-isomer. The 1,2-diketone product was produced as a byproduct.

TABLE I-continued

Ketoisophorone Synthesis Via Oxidation of Isophorone With TBHP.

| Catalyst[a] | Solvent[b] | TBHP[c] | % KIP[d] | Notes |
|---|---|---|---|---|

[f]20 mol %.
[g]13 mol %.
[h]1 mol %.
[i]4 mol %.
[j]2.5 mol %.
[k]dipyridyl, 13 mol %.
[l]Cu(II) phthalocyamine, 3 mol %.
[m]Cu(I) [Dp]$_2$ClO$_4$.

TABLE II

Ketoisophorone Via Oxidation of Isophorone With TBHP, Catalyzed With FeCl$_3$.[a]

| | Solvent[b] | TBHP[c] | % KIP[d] | Notes |
|---|---|---|---|---|
| 1 | DCE | C | 25 | not selective |
| 2 | ANP | B | 20 | air atm, rt, 2 d |
| 3 | ANP | C | 48 | O$_2$ atm, 50° C., 2 d |
| 4 | ANP | C | 45 | 3 equiv TBHP,$^e$ 50° C., 2 d |
| 5 | ANP | C | 42 | 4 equiv TBHP |
| 6 | ANP | E | 21 | add IP to TBHP/cat mixture |
| 7 | ANP | B | 30 | O$_2$ atm, 50° C., 2 d |
| 8 | ANP | B | 41 | FAS,[f] O$_2$ atm, 50° C., 2 d |
| 9 | ANP | E | 44 | O$_2$ atm, 50° C., 2 d |
| 10 | PhCl | D | nd | not selective |
| 11 | MeCN | C | nd | not selective |
| 12 | PAA | C | 36 | not selective |
| 13 | PhCN | C | nd | not selective |
| 14 | BNP | . | 37 | O$_2$ atm, 50° C. |
| 15 | ASP | C | 27 | O$_2$ atm, 50° C. |

[a]Iron salt was delivered as 4 mol % FeCl$_3$.6H$_2$O, in respect to IP.
[b]Solvents denoted as in footnote b in Table I; also, PAA = pyridine and glacial acetic acid in a 12:1 v/v ratio, resp; PhCN = benzonitrile; BNP = benzonitrile and pyridine in 4:1 v/v, resp; ASP = anisole and pyridine in 4:1 v/v resp.
[c]Same as footnote c in Table I.
[d]Yields determined by GC analysis, nd = not determined.
[e]Added after 1 d.
[f]Added 4 Angstrom molecular sieves, 5.5 g.

TABLE III

Ketoisophorone Via Oxidation of Isophorone With TBHP, Catalyzed With Various Metals.

| | Catalyst[a] | %[b] | Solvent[c] | % KIP[d] | Notes |
|---|---|---|---|---|---|
| 1 | CoCl$_2$[e] | 5 | DCE | <5 | Ar atm, heterogeneous |
| 2 | CoCl$_2$[e] | 5 | ANP | 12 | homogeneous, blue |
| 3 | PDC[f] | 5 | ANP | 25 | TBHP decomp to O$_2$ |
| 4 | PDC | 0.5 | ANP | 46 | O$_2$ atm, 50° C., 3 d |
| 5 | PDC | 0.5 | ANP | <10 | Ar atm, 3 d |
| 6 | PDC[g] | 1 | ANP | 0 | O$_2$ atm, 75° C., 5 d |
| 7 | PDC | 4 | DCE | 21 | O$_2$ atm, 50° C., 1 d |
| 8 | PCC[h] | 9 | ANP | 30 | O$_2$ atm, 50% conversion |
| 9 | Bu$_4$NMnO$_4$ | 8 | ANP | 22 | poor mass balance |
| 10 | Mn(OAc)$_2$[i] | 5 | ANP | 20 | not selective |
| 11 | RuCl$_3$[j] | 0.5 | ANP | 40 | O$_2$ atm, 70° C., 2 d |
| 12 | RuCl$_3$[j] | 0.5 | ANP | 11 | Air atm, 70° C., 2 d |
| 13 | RuCl$_3$[j] | 0.5 | MeCN | 23 | O$_2$ atm, 70° C., 2 d |
| 14 | V$_2$O$_5$ | 3 | ANP | 17 | O$_2$ atm, 50° C., 2 d |
| 15 | V$_2$O$_5$ | 5 | MeCN | 26 | Pic,[k] O$_2$ atm, 50° C., 1 d |
| 16 | V$_2$O$_5$ | 5 | MeCN | 26 | Pic,[k] O$_2$ atm, 50° C., 2 d |
| 17 | V$_2$O$_5$ | 5 | ANP | 43 | Pic,[k] O$_2$ atm, 50° C., 3 d |

[a]Catalyst was used in conjunction with a 3.3 M dried solution of TBHP (2.2 equiv) in DCE unless otherwise noted.
[b]Catalyst mol %.
[c]Solvents as denoted in footnote c in Table I.
[d]Yields determined by GC analysis.
[e]Hydrated with 6 H$_2$O.
[f](pyH)$_2$Cr$_2$O$_7$.
[g]No TBHP added.
[h](pyH)ClCrO$_3$.
[i]Hydrated with 4 H$_2$O.
[j]Hydrated with 3 H$_2$O.
[k]Picolinic acid, 20 mol %

We claim:

1. A method of making ketoisophorone which comprises reacting isophorone with a hydroperoxide in an oxidation resistant solvent and an consisting essentially of oxygen atmosphere, and in the presence of a catalyst selected from the group consisting of group IB, VB, VIB, and VIII metal catalysts.

2. The method of claim 1 wherein the solvent comprises at least one component selected from the group consisting of toluene, cumene, acetonitrile, chlorobenzene, 1,2-dichloroethane, chloroform, pyridine picolinic acid and methylene chloride.

3. The method of claim 1 wherein the solvent comprises at least one component selected from the group consisting of toluene, cumene, acetonitrile, chlorobenzene, chloroform, picolinic acid and pyridine.

4. The method of claim 1 wherein the hydroperoxide is TBHP.

5. The method of claim 1 wherein said hydroperoxide is an azeotropically dried solution.

6. The method of claim 1 wherein said solvent comprises pyridine which is 10 to 100 vol % of said solvent.

7. The method of claim 1 wherein the solvent is a mixture comprising pyridine and acetonitrile.

8. The method of claim 7 wherein about 10 to 30 vol% of the mixture is pyridine.

9. The method of claim 1 wherein an isophorone to hydroperoxide ratio is from about 2 to 4:1.

10. The method of claim 1 wherein an isophorone to hydroperoxide ratio is about 2.2 to 2.4:1.

11. The method of claim 1 wherein the hydroperoxide is added in a concentration of about 5 mol/L or less.

12. The method of claim 1 wherein the hydroperoxide is added in a concentration of about 3.0 to 3.3 mol/L.

13. The method of claim 1 wherein the catalyst is selected from the group consisting of CuCl, Cu(II) phthalocyamine, Cu(I) [dipyridyl]$_2$ClO$_4$, RuCl$_3$.3H$_2$O, V$_2$O$_5$, PDC, and FeCl$_3$.

* * * * *

UNITED STATES PATENT AND TRADEMARK OFFICE
CERTIFICATE OF CORRECTION

PATENT NO. : 5,545,761
DATED : August 13, 1996
INVENTOR(S) : Dawson et al.

It is certified that error appears in the above-identified patent and that said Letters Patent is hereby corrected as shown below:

Column 3, line 11 after "quantities" add "of".

Column 6, line 23 after "an" add "atmosphere".

Column 6, line 24 delete "atmosphere".

Signed and Sealed this

First Day of April, 1997

*Attest:*

BRUCE LEHMAN

*Attesting Officer*  *Commissioner of Patents and Trademarks*